(12) United States Patent
Biedermann et al.

(10) Patent No.: US 9,539,035 B2
(45) Date of Patent: Jan. 10, 2017

(54) ROD INSERTION DEVICE

(71) Applicant: BIEDERMANN TECHNOLOGIES GMBH & CO. KG, Donaueschingen (DE)

(72) Inventors: Timo Biedermann, Trossingen (DE); Berthold Dannecker, St. Georgen (DE)

(73) Assignee: Biedermann Technologies GmbH & Co. KG, Donaueschingen (DE)

( * ) Notice: Subject to any disclaimer, the term of this patent is extended or adjusted under 35 U.S.C. 154(b) by 0 days.

(21) Appl. No.: 14/578,143

(22) Filed: Dec. 19, 2014

(65) Prior Publication Data

US 2015/0173810 A1    Jun. 25, 2015

Related U.S. Application Data

(60) Provisional application No. 61/919,559, filed on Dec. 20, 2013.

(30) Foreign Application Priority Data

Dec. 20, 2013   (EP) .................................... 13199223

(51) Int. Cl.
   *A61B 17/70*      (2006.01)
   *A61B 17/56*      (2006.01)

(52) U.S. Cl.
   CPC ....... *A61B 17/7088* (2013.01); *A61B 17/7004* (2013.01); *A61B 17/7089* (2013.01); *A61B 17/7011* (2013.01); *A61B 2017/564* (2013.01); *A61B 2090/034* (2016.02); *A61B 2090/037* (2016.02)

(58) Field of Classification Search
   CPC .................................. A61B 17/7083–17/7089
   USPC ........................................ 606/86 A, 99, 279
   See application file for complete search history.

(56) References Cited

U.S. PATENT DOCUMENTS

| 6,332,780 B1 * | 12/2001 | Traxel ............... A61B 17/7083 434/267 |
| 7,918,878 B2 | 4/2011 | Songer et al. |
| 8,105,362 B2 | 1/2012 | Duarte |
| 8,157,806 B2 * | 4/2012 | Frigg .................. A61B 17/025 606/246 |

(Continued)

OTHER PUBLICATIONS

European Search Report dated Jun. 5, 2014, Application Serial No. 13199223.2, 9 sheets.

*Primary Examiner* — Eduardo C Robert
*Assistant Examiner* — Michelle C Eckman
(74) *Attorney, Agent, or Firm* — Lewis Roca Rothgerber Christie LLP

(57) ABSTRACT

A rod insertion system and at least two bone anchors including: a rod guide configured to accommodate a spinal stabilization rod therein; a holding device including a clamping portion configured to hold a portion of the rod guide; and an adapter configured to moveably support the holding device. The holding device is configured to move and pivot along an adapter such that the rod guide is positioned proximal to a rod channel of one of the at least two bone anchors. In a first state, the rod guide is fixed to the holding device by the clamping portion, and, in a second state in which the holding device supports the portion of the rod guide, the clamping portion is released from the portion of the rod guide to permit the orientation of the rod guide relative to the holding device to be polyaxially adjusted.

31 Claims, 13 Drawing Sheets

(56) References Cited

U.S. PATENT DOCUMENTS

Figure 1:
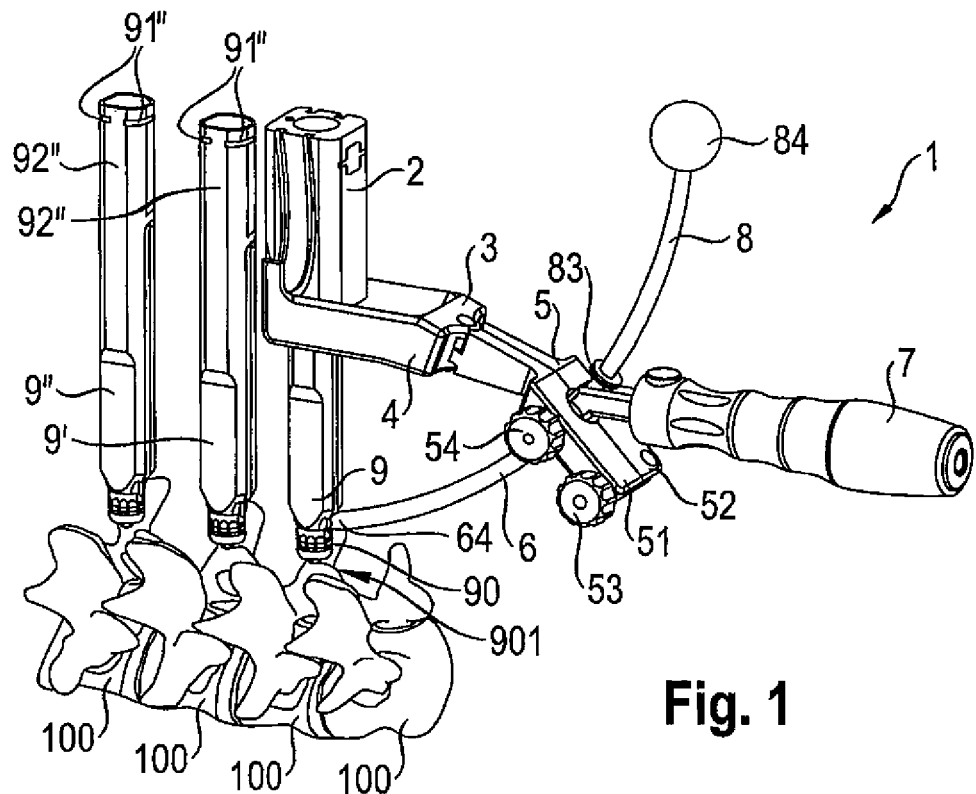

| | | | | |
|---|---|---|---|---|
| 8,187,282 B2* | 5/2012 | Tornier | A61B 17/1739 | 606/99 |
| 8,221,426 B2* | 7/2012 | Justis | A61B 17/708 | 606/86 A |
| 8,287,546 B2* | 10/2012 | King | A61B 17/7037 | 606/105 |
| 8,419,744 B2* | 4/2013 | Petit | A61F 2/4611 | 606/99 |
| 8,690,920 B2* | 4/2014 | Perez-Cruet | A61B 17/7065 | 606/249 |
| 8,840,621 B2* | 9/2014 | Farr | A61B 17/025 | 606/99 |
| 8,882,807 B2* | 11/2014 | Cawley | A61B 17/7085 | 606/264 |
| 2002/0161368 A1* | 10/2002 | Foley | A61B 17/1671 | 128/898 |
| 2003/0208203 A1* | 11/2003 | Lim | A61B 17/7083 | 606/86 A |
| 2004/0215190 A1* | 10/2004 | Nguyen | A61B 17/1671 | 606/86 A |
| 2005/0070917 A1* | 3/2005 | Justis | A61B 17/1757 | 606/104 |
| 2005/0171540 A1* | 8/2005 | Lim | A61B 17/7005 | 606/86 A |
| 2005/0197660 A1* | 9/2005 | Haid, Jr. | A61B 17/7064 | 606/86 A |
| 2005/0234449 A1 | 10/2005 | Aferzon | | |
| 2005/0277934 A1* | 12/2005 | Vardiman | A61B 17/7083 | 606/914 |
| 2006/0009775 A1* | 1/2006 | Dec | A61B 17/7088 | 606/86 R |
| 2006/0030839 A1* | 2/2006 | Park | A61B 17/7032 | 606/1 |
| 2006/0111728 A1* | 5/2006 | Abdou | A61F 2/4611 | 606/86 R |
| 2006/0122597 A1* | 6/2006 | Jones | A61B 17/7091 | 606/86 A |
| 2006/0149238 A1* | 7/2006 | Sherman | A61B 17/7031 | 606/254 |
| 2006/0149278 A1* | 7/2006 | Abdou | A61B 17/7077 | 606/90 |
| 2006/0271050 A1* | 11/2006 | Piza Vallespir | A61B 17/7085 | 606/86 A |
| 2007/0049931 A1* | 3/2007 | Justis | A61B 17/7089 | 606/86 A |
| 2007/0112351 A1* | 5/2007 | Assell | A61B 17/1735 | 606/86 A |
| 2007/0270819 A1* | 11/2007 | Justis | A61B 17/701 | 606/279 |
| 2007/0270867 A1* | 11/2007 | Miller | A61B 17/7088 | 606/86 R |
| 2007/0270869 A1* | 11/2007 | Young | A61B 17/7086 | 606/86 R |
| 2007/0288026 A1* | 12/2007 | Shluzas | A61B 17/02 | 606/86 A |
| 2008/0051782 A1* | 2/2008 | Wu | A61B 17/7089 | 606/250 |
| 2008/0221586 A1* | 9/2008 | Garcia-Bengochea | A61B 17/02 | 606/108 |
| 2008/0234678 A1* | 9/2008 | Gutierrez | A61B 17/7086 | 606/60 |
| 2008/0243052 A1* | 10/2008 | Pond | A61B 17/7083 | 604/28 |
| 2008/0249531 A1* | 10/2008 | Patterson | A61B 17/7089 | 606/99 |
| 2008/0319477 A1* | 12/2008 | Justis | A61B 17/7089 | 606/232 |
| 2009/0012568 A1* | 1/2009 | Farr | A61B 17/025 | 606/279 |
| 2009/0036895 A1* | 2/2009 | Marino | A61B 17/7079 | 606/90 |
| 2009/0062857 A1* | 3/2009 | Ramsay | A61B 17/1735 | 606/246 |
| 2009/0062858 A1* | 3/2009 | Dziedzic | A61B 17/7089 | 606/278 |
| 2009/0326586 A1* | 12/2009 | Duarte | A61B 17/7089 | 606/264 |
| 2010/0030065 A1* | 2/2010 | Farr | A61B 17/025 | 600/424 |
| 2010/0076502 A1* | 3/2010 | Guyer | A61B 17/02 | 606/86 R |
| 2010/0121386 A1* | 5/2010 | Peultier | A61B 17/7086 | 606/86 A |
| 2011/0087291 A1* | 4/2011 | Justis | A61B 17/7004 | 606/264 |
| 2011/0112586 A1* | 5/2011 | Guyer | A61B 17/0293 | 606/86 A |
| 2011/0152942 A1* | 6/2011 | Oh | A61B 17/7002 | 606/279 |
| 2011/0152952 A1* | 6/2011 | Oh | A61B 17/7085 | 606/86 A |
| 2011/0184464 A1* | 7/2011 | Fiorella | A61B 17/7089 | 606/264 |
| 2011/0190820 A1* | 8/2011 | Johansson | A61B 17/7077 | 606/264 |
| 2011/0218581 A1* | 9/2011 | Justis | A61B 17/708 | 606/86 A |
| 2012/0083853 A1* | 4/2012 | Boachie-Adjei | A61B 17/7038 | 606/86 A |
| 2012/0109208 A1* | 5/2012 | Justis | A61B 17/7032 | 606/264 |
| 2012/0130429 A1* | 5/2012 | Mitchell | A61B 17/7004 | 606/259 |
| 2012/0143269 A1* | 6/2012 | Ichelmann | A61B 17/7082 | 606/86 R |
| 2012/0271355 A1* | 10/2012 | Steele | A61B 17/7008 | 606/264 |
| 2012/0323278 A1* | 12/2012 | Tsuang | A61B 17/1671 | 606/264 |
| 2012/0323279 A1* | 12/2012 | Tsuang | A61B 17/7002 | 606/279 |
| 2013/0035726 A1 | 2/2013 | Nguyen et al. | | |
| 2013/0090691 A1* | 4/2013 | Zhang | A61B 17/7001 | 606/264 |
| 2013/0096637 A1* | 4/2013 | Richelsoph | A61B 17/7089 | 606/86 A |
| 2013/0245692 A1* | 9/2013 | Hayes | A61B 17/025 | 606/279 |
| 2014/0039556 A1* | 2/2014 | Rutschmann | A61B 17/7002 | 606/266 |
| 2014/0128930 A1* | 5/2014 | Meyer | A61B 17/7083 | 606/86 A |
| 2014/0228899 A1* | 8/2014 | Thoren | A61B 17/885 | 606/86 R |
| 2014/0249592 A1* | 9/2014 | Black | A61B 17/7004 | 606/86 A |
| 2014/0257416 A1* | 9/2014 | Meyer | A61B 17/7083 | 606/86 A |
| 2014/0277196 A1* | 9/2014 | Foley | A61B 17/1757 | 606/86 A |
| 2014/0277205 A1* | 9/2014 | Stein | A61B 17/7086 | 606/86 A |
| 2014/0379032 A1* | 12/2014 | Hennard | A61B 17/56 | 606/279 |
| 2015/0039035 A1* | 2/2015 | Kruger | A61B 17/7037 | 606/264 |
| 2015/0045834 A1* | 2/2015 | McBride | A61B 17/7077 | 606/264 |
| 2015/0057712 A1* | 2/2015 | Hsueh | A61B 17/7074 | 606/86 A |
| 2015/0100099 A1* | 4/2015 | Kitagawa | A61B 17/3403 | 606/86 A |

(56) References Cited

U.S. PATENT DOCUMENTS

| | | | |
|---|---|---|---|
| 2015/0157367 A1* | 6/2015 | Biedermann | A61B 17/7004 606/279 |
| 2015/0173810 A1* | 6/2015 | Biedermann | A61B 17/7088 606/279 |
| 2015/0209156 A1* | 7/2015 | Greenhalgh | A61B 17/00234 606/80 |

* cited by examiner

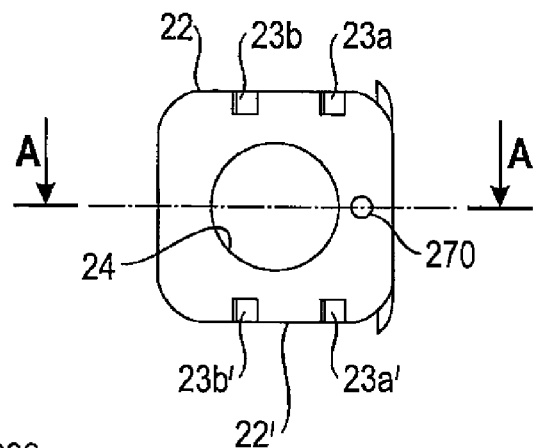
Fig. 3
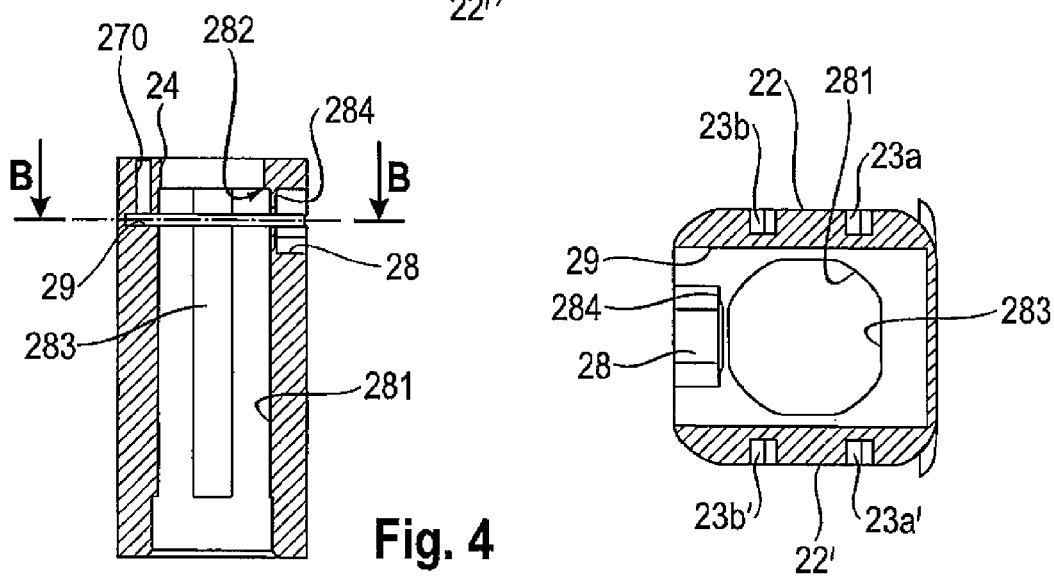
Fig. 4
Fig. 5
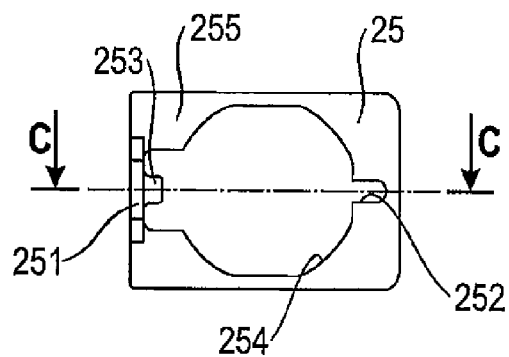
Fig. 6
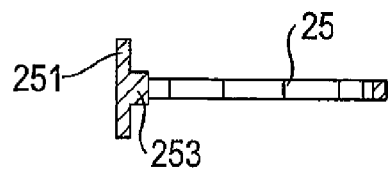
Fig. 7

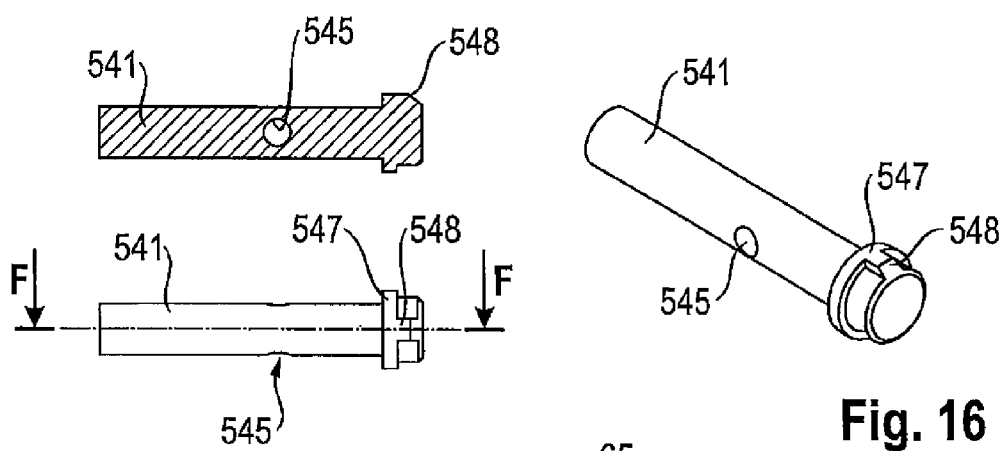
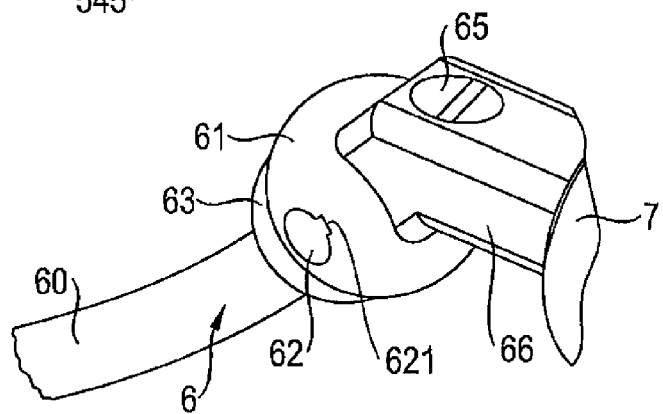
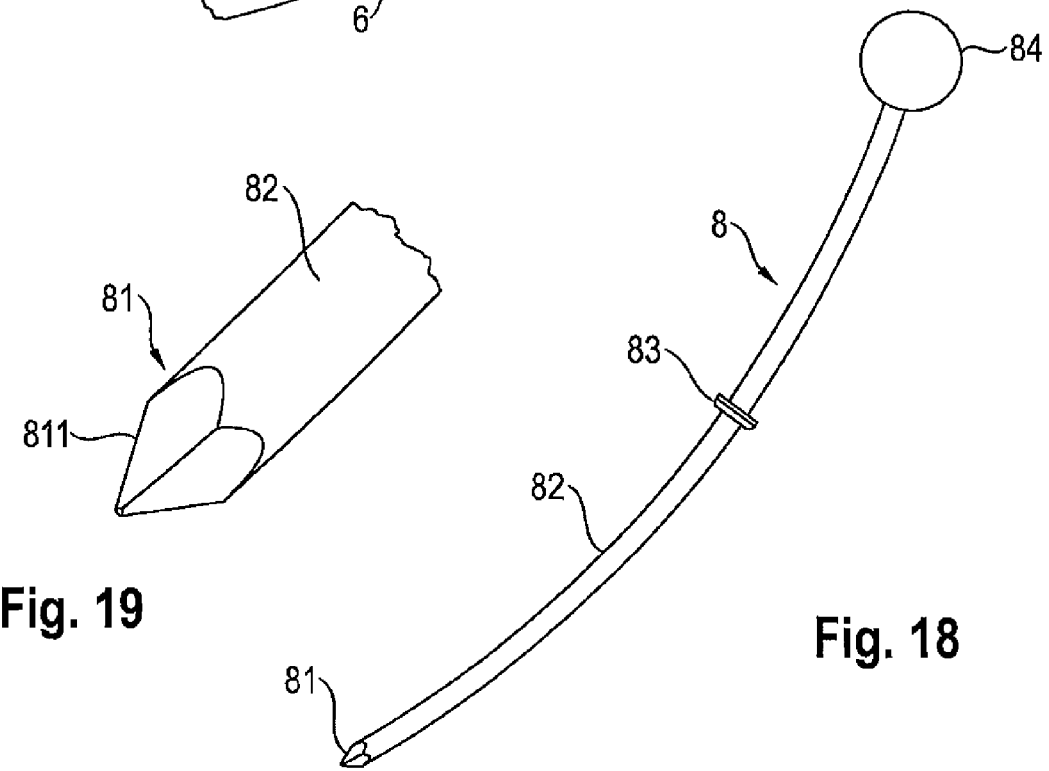

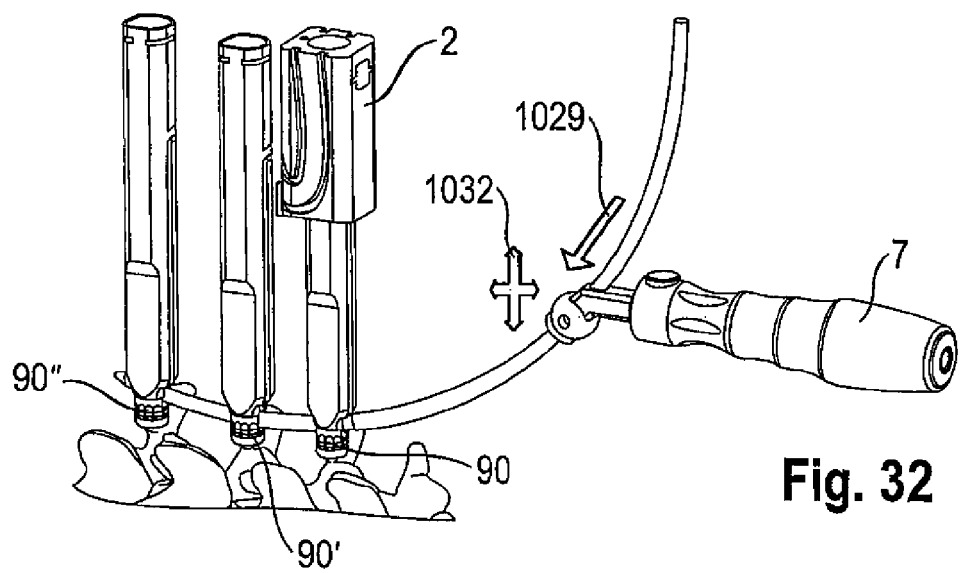
Fig. 32
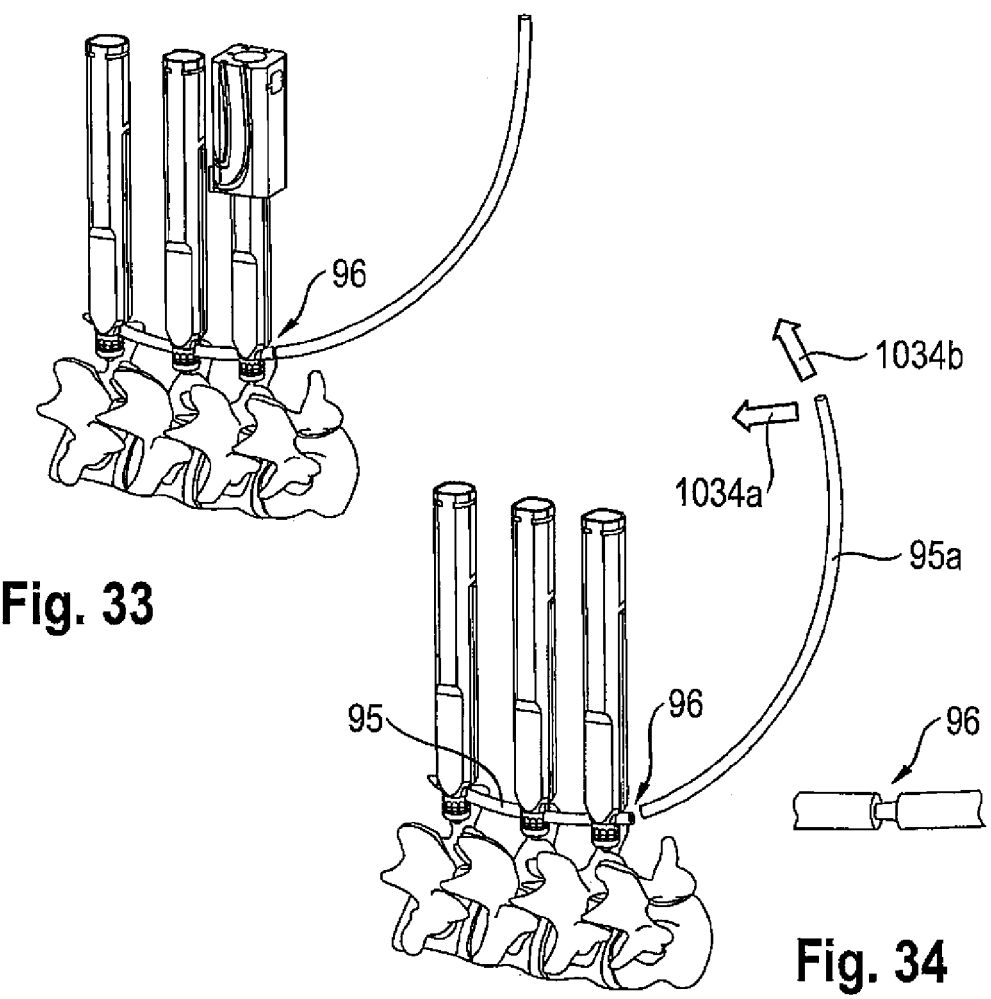
Fig. 33
Fig. 34

ROD INSERTION DEVICE

CROSS-REFERENCE TO RELATED APPLICATIONS

The present disclosure claims the benefit of U.S. Provisional Patent Application Ser. No. 61/919,559, filed on Dec. 20, 2013, the contents of which are hereby incorporated by reference in their entirety, and claims priority to European Patent Application EP 13199223.2, filed on Dec. 20, 2013, the contents of which are hereby incorporated by reference in their entirety.

BACKGROUND

Field of the Invention

The present invention relates to a rod insertion device for inserting a spinal stabilization rod into at least two bone anchors. The device includes a tubular rod guide that allows the spinal stabilization rod to move therethrough, a holding device configured to hold the rod guide, and an adapter configured to be connected to an extension which may be fixed to a receiving part of one of the bone anchors.

Description of the Related Art

It is known in the art to treat fractures of the spinal column, arthrodesis, scoliosis, etc. by stabilizing the spinal column using bone anchors implanted in two or more vertebrae and connecting the same by rigid or dynamically flexible stabilization rods to, for example, define a predetermined relative position and movement tolerance for each of the vertebrae involved. In operation, bone anchors are selectively provided to vertebrae and a stabilization rod is then used (e.g., inserted) to connect each of the bone anchors. Several methods and instruments have been developed to insert a rod into respective rod channels provided in receiving parts of the bone anchors.

U.S. 2013/0096637 A1 discloses an instrument having a main body holding a tubular, curved rod holder which receives a rod. The rod can be advanced through slots of respective spinal implants. An extension at the main body functions as an adapter to connect to a post which is mounted to the receiving part of a spinal implant (e.g., a bone anchor). Keyways provided at the post and extension ensure that the main body attains a predetermined position with respect to the spinal implant. In operation, a handle is used to advance the rod holder with the rod mounted therein through the soft-tissue until a predetermined position proximal to a slot in the spinal implant is reached. Thereby, a set of bearings are provided in the main body which guide the rod holder.

U.S. 2002/0161368 A1 discloses an installation instrument for a connecting element (e.g., a rod) including support arms that respectively connect to anchor extensions mounted to yokes of two adjacent bone anchors. An inserter for the rod is provided as a pivot arm which may pivot in a circular manner about an axis relative to the support arms. As a consequence, the rod is inserted into respective passage ways of the adjacent anchors by the pivoting movement of the inserter.

U.S. Pat. No. 8,105,362 B2 discloses a rod insertion system. Extenders mounted at respective pedicle screw heads are provided with extender heads which are aligned with respect to each other using rod-like alignment members. The alignment members are slidably engaged with a pair of arms which securely connect to an arcuate guide tube. The arcuate guide tube holds an insertion member by which a spinal rod may be advanced through respective passageways of the pedicle screws using a rod insertion probe.

U.S. Pat. No. 7,918,878 B2 discloses a minimally invasive surgical (MIS) system, wherein an inserter formed as a straight rod is held by a guide. The inserter is provided with a connecting member at its tip. The guide is connected to a manipulator assembly extending from a bone anchor, and the guide has an aperture through which the inserter is led such as to deposit the connecting member in an accurate position in passageways of two adjacent bone anchors. The aperture may be opened to release the inserter.

SUMMARY

It is an object of the invention to improve systems and methods of inserting a rod into rod channels of at least two bone anchors in minimally invasive surgery (MIS). More specifically, it is an object to simplify the process of inserting a rod and to thereby increase the flexibility for an operator.

According to embodiments of the invention, a rod insertion device is provided including a tubular rod guide, a holding device configured to hold (e.g., support) the rod guide, and an adapter configured to be connected to an extension which may be mounted to a receiving part of a bone anchor. The adapter is configured to movably support the holding device. Consequently, the adapter allows the holding device and the rod guide to move and pivot along a predetermined path such that a front portion of the rod guide reaches a desired position proximal to a rod channel of the first receiving part of a first bone anchor to which the extension may be mounted.

The coordinated movement of the holding device and the rod guide is ensured by a clamping device which is configured to clamp a portion of the rod guide. An advantage arises in that the clamping device is also configured to selectively release the rod guide in the above described state, that is, when the front portion of the rod guide has entered the soft tissue under MIS conditions and is positioned proximal to the rod channel of the receiving part. Such release is provided in such a way that an orientation of the rod guide may be adjusted (e.g., corrected) in a polyaxial manner. In other words, the rod guide may be rotated as well as pivoted in this state.

According to one specific embodiment, two distinct release states of the rod guide from the holding device may be realized. Therein, a full release is achieved by arranging the clamping portion such that the rod guide can be removed from the clamping portion. In this state, the rod guide is separated from the holding device but substantially maintains its position and orientation with the front portion positioned proximal to the receiving part since it will already be within the soft tissue when this release occurs. This may be achieved, for example, by arranging the clamping section in multiple distinct parts connected via a first locking arrangement which allows separation of respective parts and, thus, their removal.

The other state of release is realized by a second locking arrangement provided at the clamping portion. Herein, a partial release is achieved, which means that a portion of the rod guide is still held by the clamping portion, but a re-orientation of the rod guide becomes possible in a polyaxial manner. One specific example may be the provision of a ball-joint or swivel head mechanism for the connection between the portion of the rod guide to be clamped and the clamping portion, but other mechanisms achieving the polyaxial re-orientation may be possible as well.

In this state, the rod guide is still securely held (e.g., supported) but small corrections to the orientation thereof are possible.

Nevertheless, embodiments of the invention are possible in which only one of the two release states as described above is achievable.

Another specific embodiment of the invention relates to the provision of a dedicated support structure for the adapter by which the holding device is moved such that the front portion of the rod guide attains its position proximal to the rod channel of the receiving part. The support structure provides for an initial translational (e.g., substantially linear) movement of the rod guide followed by a smooth transition towards a pivoting movement, allowing, for example, the curved rod guide to be introduced closer to the bone anchor which further reduces the harm for the patient. Such a support structure may be realized, for example, by a cam-like structure such as pins which slide in grooves, but other mechanisms using rods connected via hinges, joints, and rotation axes may be possible as well.

BRIEF DESCRIPTIONS OF THE DRAWINGS

Figure 2:
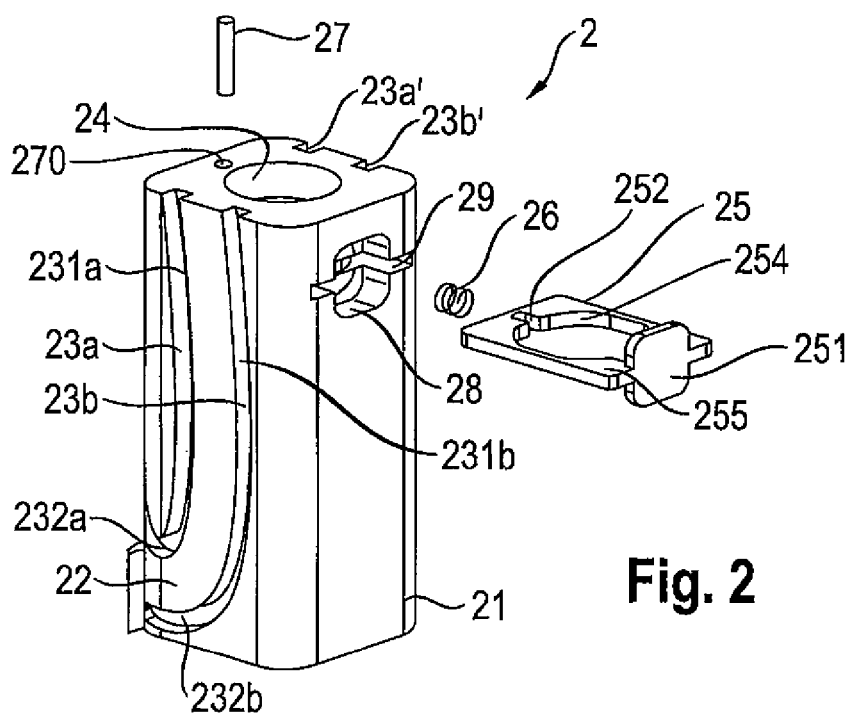
Figure 8:
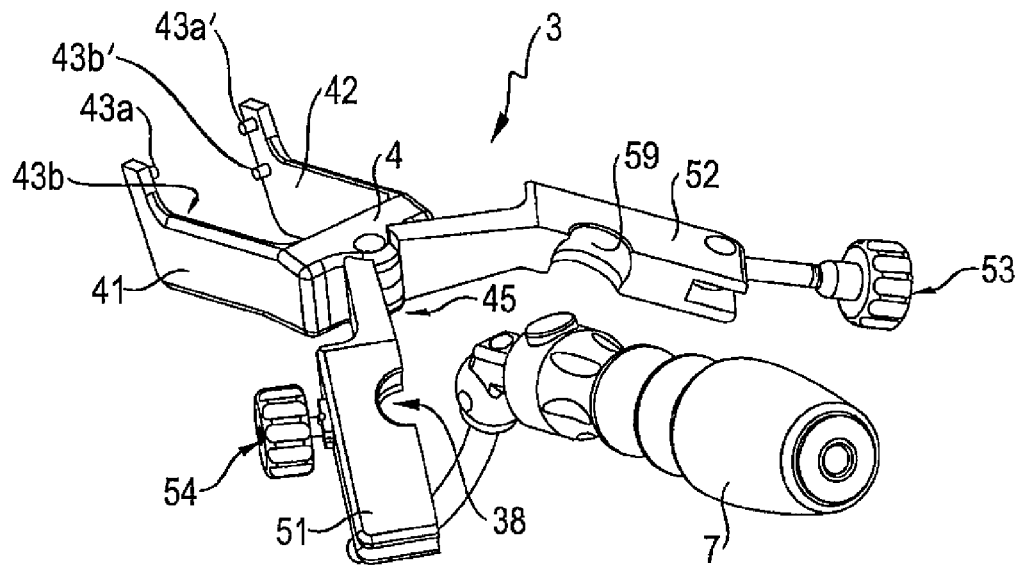
Figure 9:
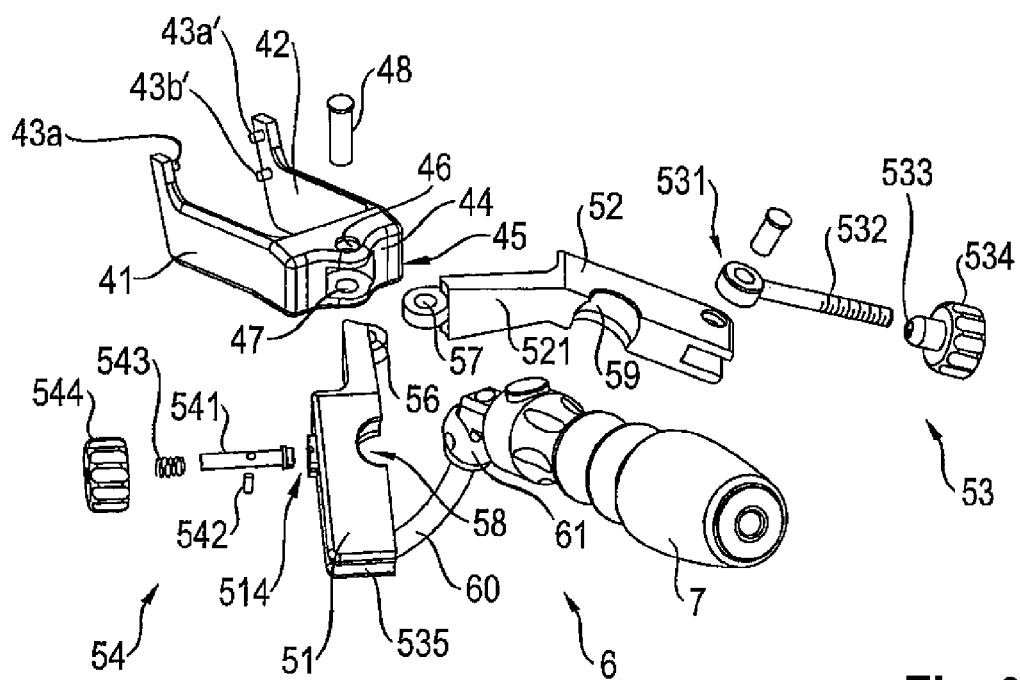
Figure 10:
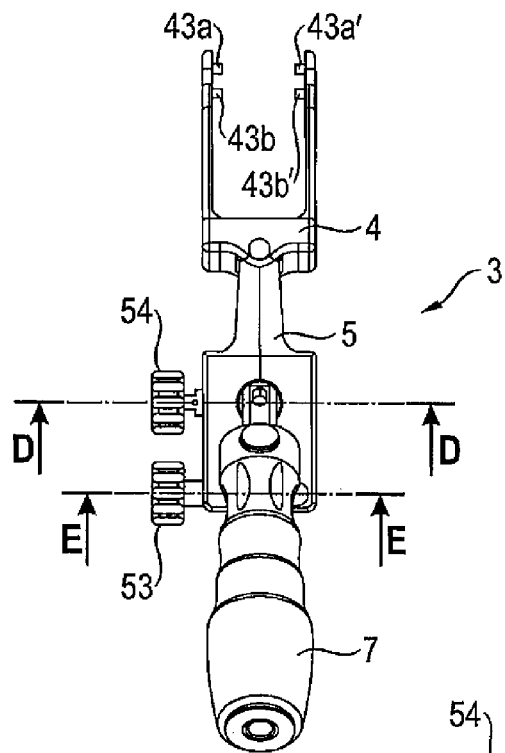
Figure 11:
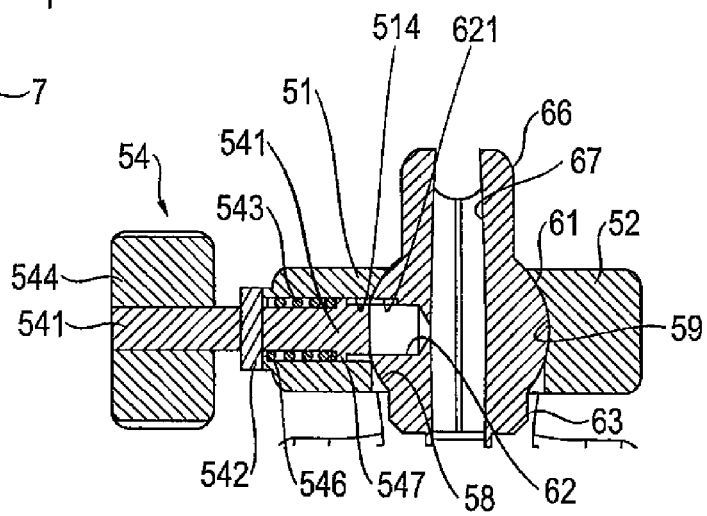
Figure 12:
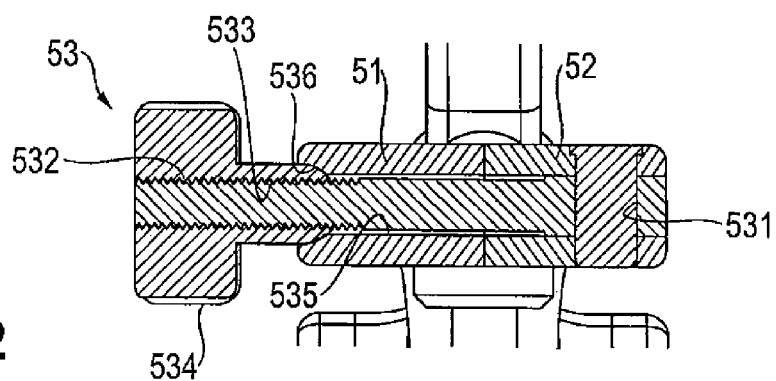
Figure 13:
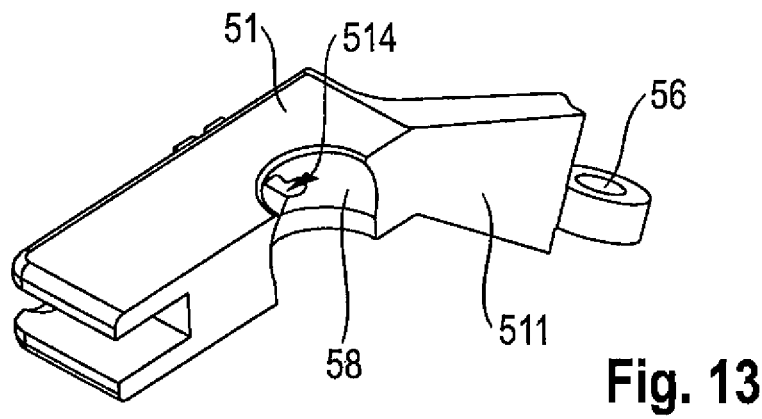
Figure 14:
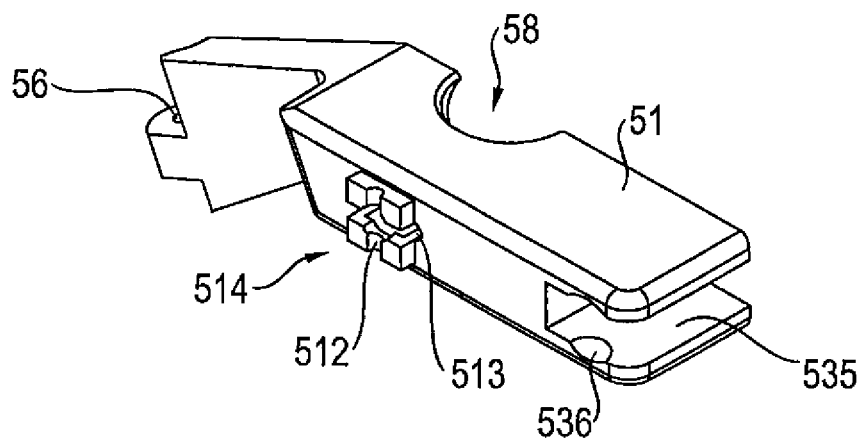
Figure 15:
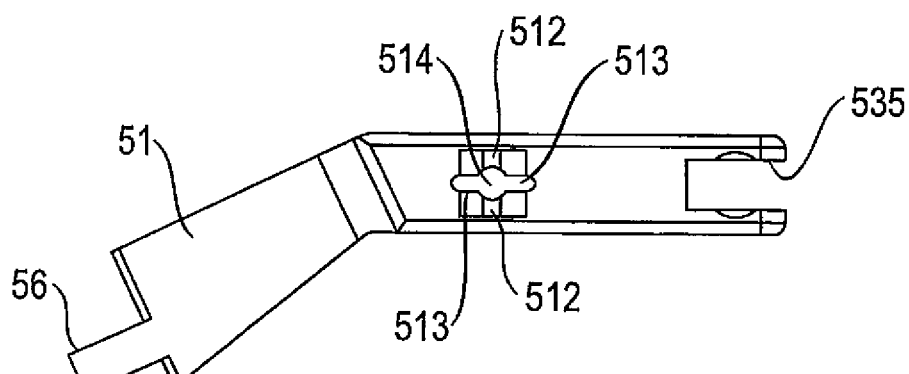
Figure 20:
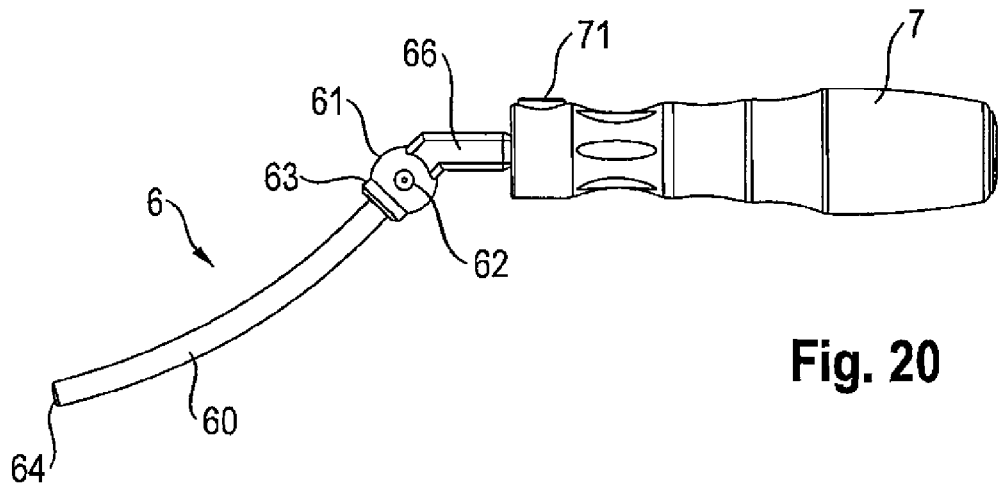
Figure 21:
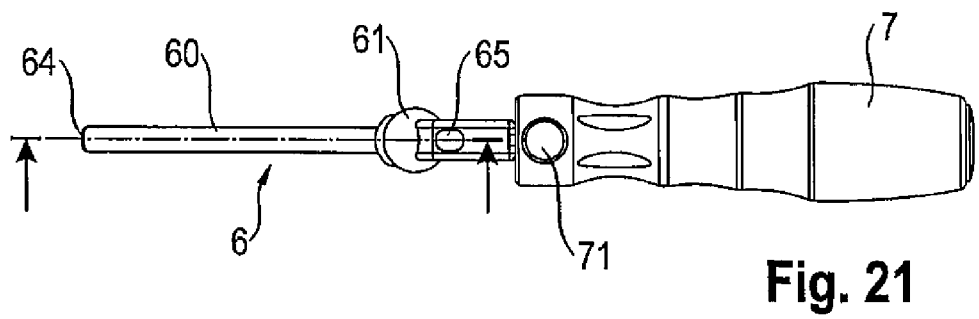
Figure 22:
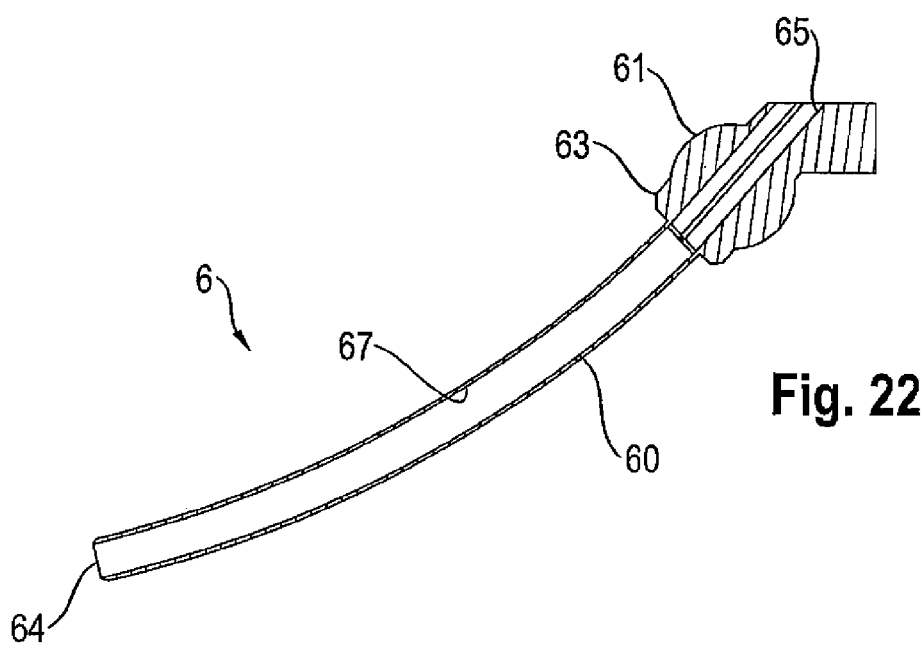
Figure 23:
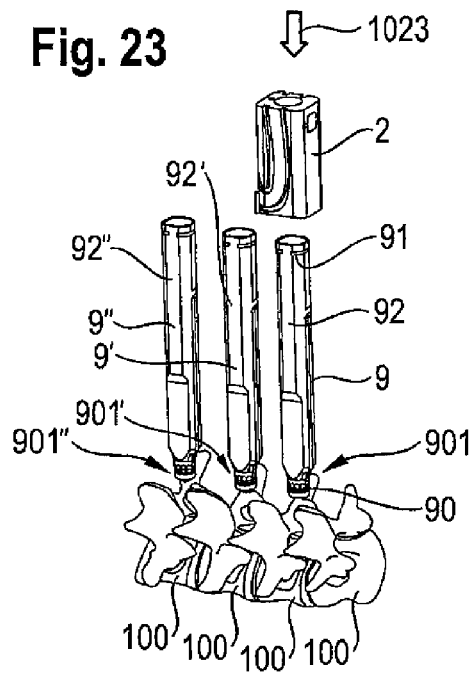
Figure 24:
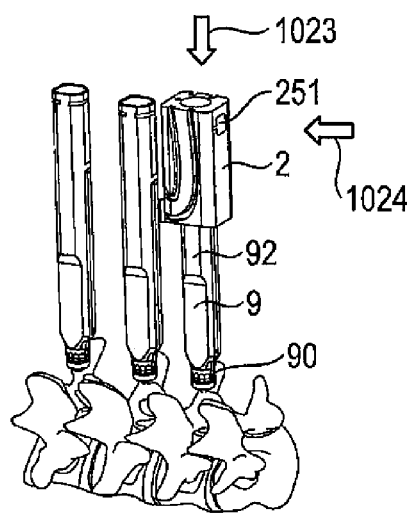
Figure 25:
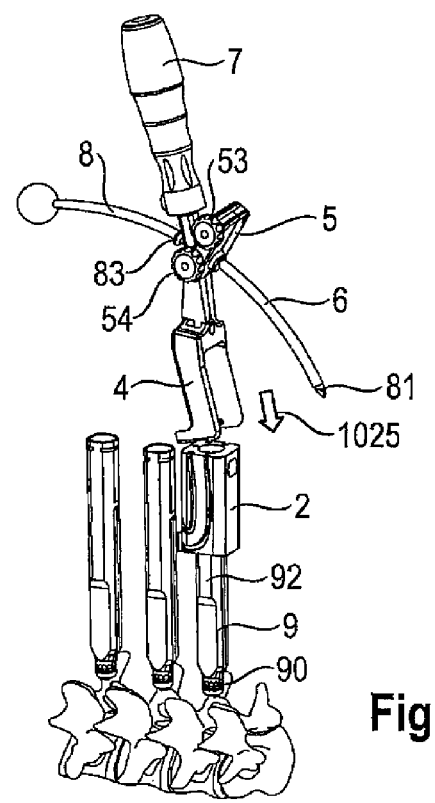
Figure 26:
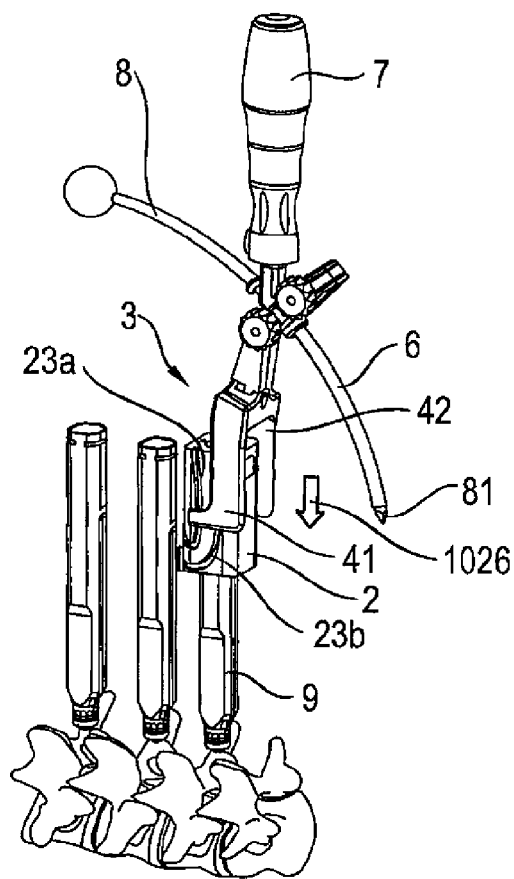
Figure 27:
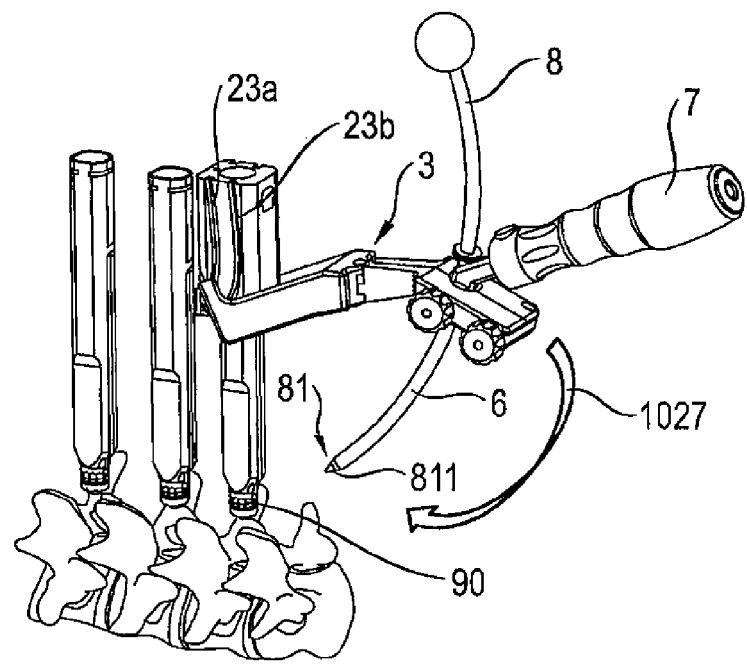
Figure 28:
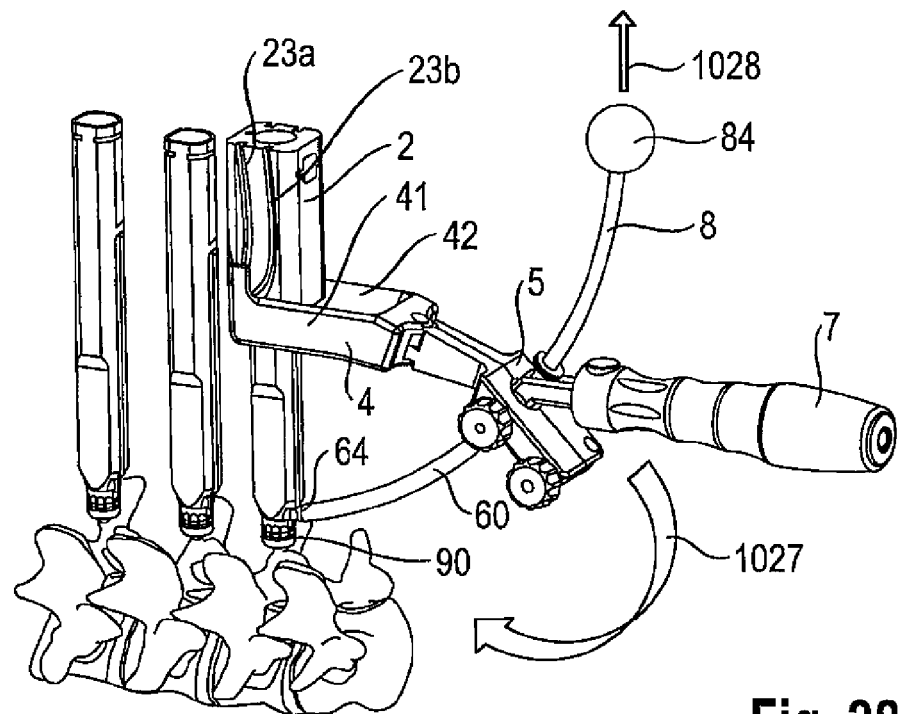
Figure 29:
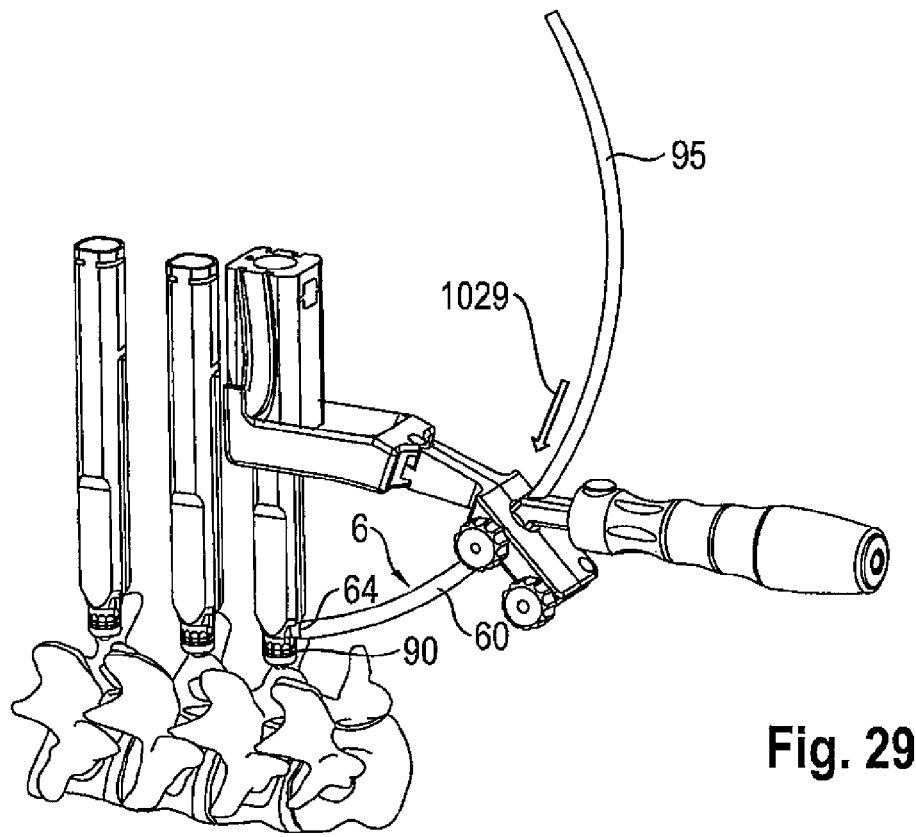
Figure 30:
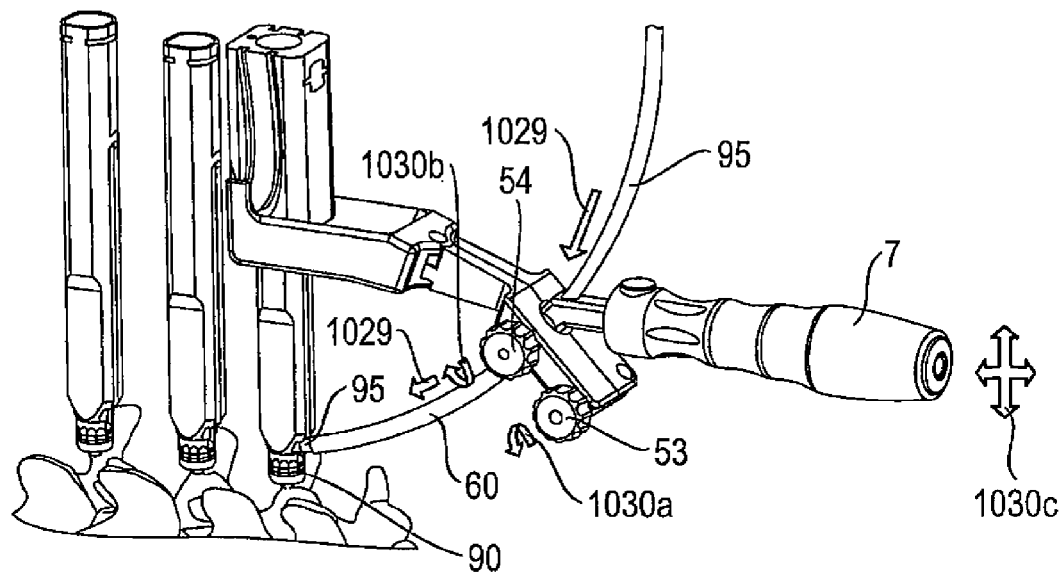
Figure 31:
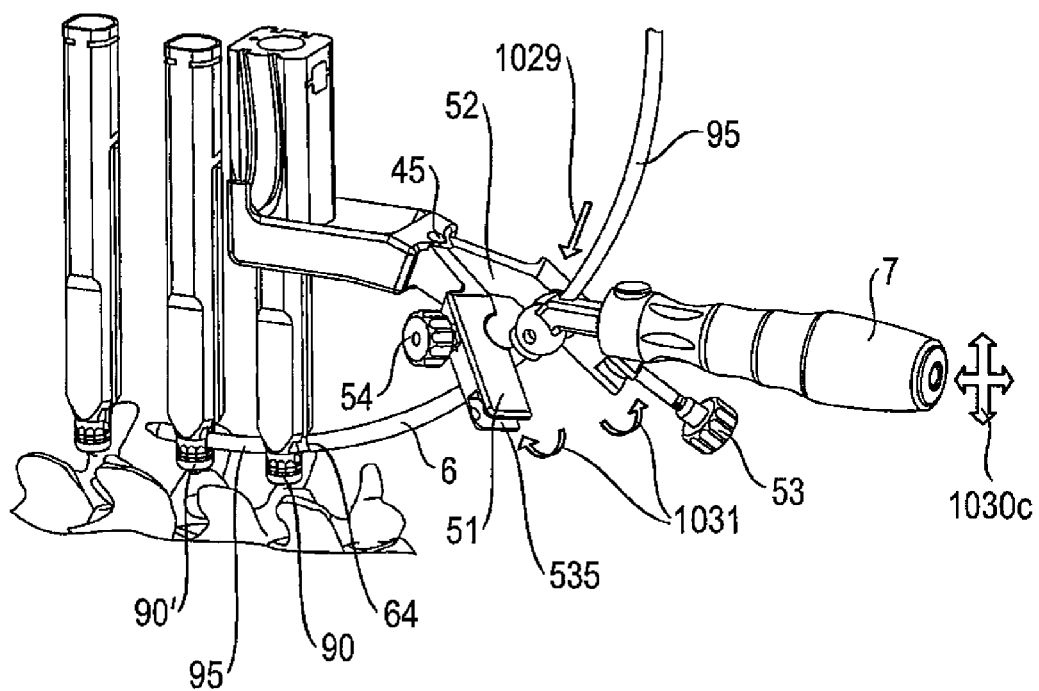
Figure 35:
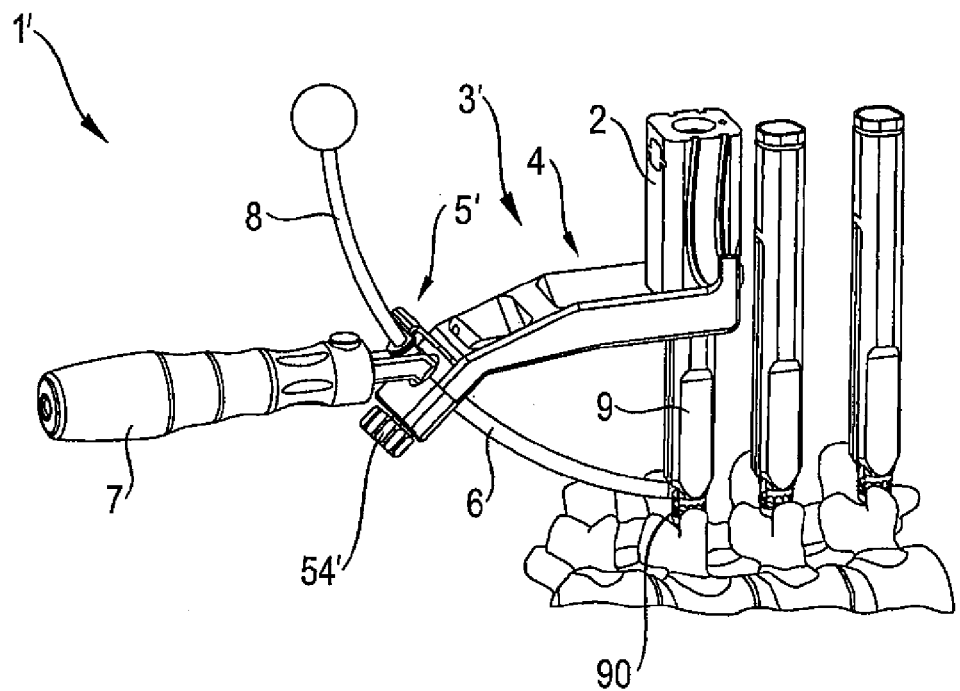
Figure 36:
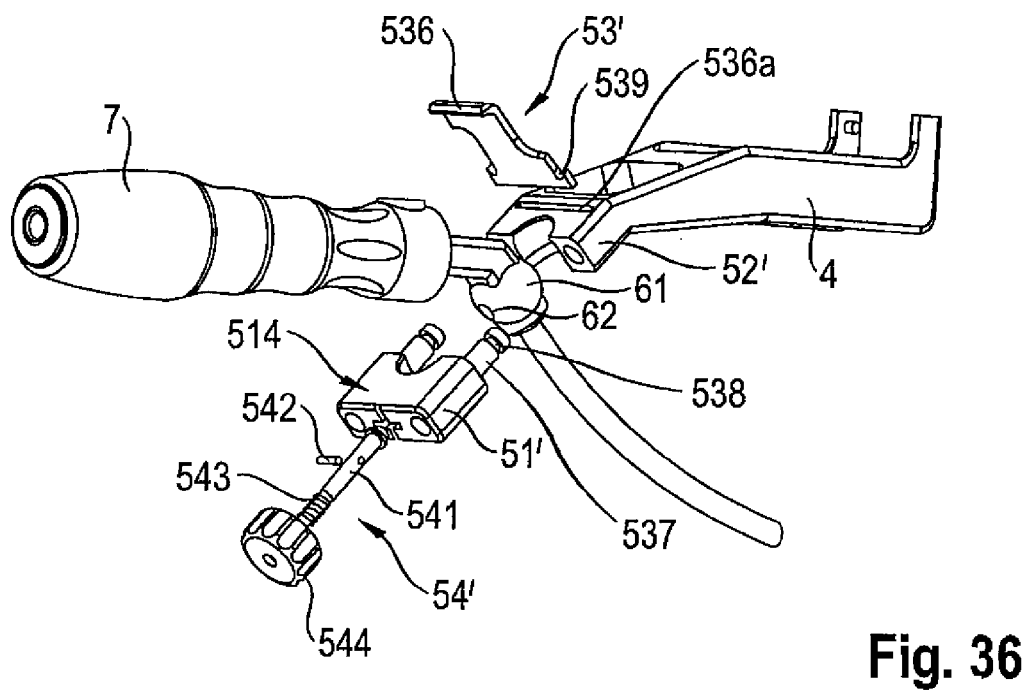

The invention will now be described with respect to embodiments taken in conjunction with the accompanying drawings. In the drawings:

FIG. 1: shows an overview of a rod insertion device according to a first embodiment in a state in which the rod insertion device is attached to an adapter which is attached to an extension mounted to a receiving part of a bone anchor;

FIG. 2: shows an exploded perspective view of the adapter shown in FIG. 1;

FIG. 3: shows a top view of the adapter of FIG. 2;

FIG. 4: shows a cross-sectional view along a plane A-A of the adapter in FIG. 3;

FIG. 5: shows a cross-sectional view along a plane B-B of the adapter in FIG. 4;

FIG. 6: shows a top view of a securing plate for the adapter shown in FIG. 2;

FIG. 7: shows a cross-sectional view along a plane C-C of the securing plate in FIG. 6;

FIG. 8: shows a perspective view of the holding device and the rod guide with a handle of the rod insertion device shown in FIG. 1;

FIG. 9: shows an exploded view of the parts shown in FIG. 8;

FIG. 10: shows an illustrative top view of the parts shown in FIG. 8;

FIG. 11: shows a cross-sectional view of details of a second locking arrangement along a plane D-D shown in FIG. 10;

FIG. 12: shows a cross-sectional view of details of a first locking arrangement along a plane E-E shown in FIG. 10;

FIG. 13: shows a perspective view of a left side bracket shown in FIGS. 8 and 9;

FIG. 14: shows the left side bracket of FIG. 13 but from another viewpoint;

FIG. 15: shows the left side bracket of FIG. 13 but from yet another viewpoint;

FIG. 16: shows a cross-sectional view, a top view, and a perspective view of a pin of the second locking arrangement shown in FIG. 9;

FIG. 17: shows an enlarged portion of a clamped portion of the rod guide of FIG. 1;

FIG. 18: shows a side view of a cutting piece received by the rod guide shown in FIG. 1;

FIG. 19: shows an enlarged portion of a tip of the cutting piece of FIG. 18;

FIG. 20: shows a side view of the rod guide with the handle shown in FIG. 1;

FIG. 21: shows a top view of the rod guide with the handle of FIG. 20;

FIG. 22: shows a cross-sectional side view of the rod guide of FIGS. 20 and 21;

FIG. 23: shows a first step of a method of using the rod insertion device according to the first embodiment;

FIG. 24: shows a second step of the method of using the rod insertion device according to the first embodiment;

FIG. 25: shows a third step of the method of using the rod insertion device according to the first embodiment;

FIG. 26: shows a fourth step of the method of using the rod insertion device according to the first embodiment;

FIG. 27: shows a fifth step of the method of using the rod insertion device according to the first embodiment;

FIG. 28: shows a sixth step of the method of using the rod insertion device according to the first embodiment;

FIG. 29: shows a seventh step of the method of using the rod insertion device according to the first embodiment;

FIG. 30: shows an eighth step of the method of using the rod insertion device according to the first embodiment;

FIG. 31: shows a ninth step of the method of using the rod insertion device according to the first embodiment;

FIG. 32: shows a tenth step of the method of using the rod insertion device according to the first embodiment;

FIG. 33: shows an eleventh step of the method of using the rod insertion device according to the first embodiment;

FIG. 34: shows a twelfth step of the method of using the rod insertion device according to the first embodiment;

FIG. 35: shows an overview of a rod insertion device according to a second embodiment of the invention in a perspective view, and the rod insertion device is shown attached to an extension mounted on a receiving part of the bone anchor;

FIG. 36: shows an exploded view of the rod insertion device of FIG. 35 without the adapter and the inner cutting piece.

DETAILED DESCRIPTION

A first embodiment of a rod insertion device according to the invention will be described with respect to FIGS. 1 through 22, and a corresponding method of using the rod insertion device according to the first embodiment will be described with respect to FIGS. 23 through 34.

An overview of the rod insertion device 1 according to the first embodiment is shown in FIG. 1. The main parts of the rod insertion device 1 are an adapter 2, a holding device 3 including a base portion 4 and a clamping portion 5, a rod guide 6 with handle 7, and a removable inner cutting piece 8. The rod insertion device 1 of this embodiment is applied to a series of extensions 9, 9', 9" with each extension mounted to a respective receiving part 90 of a bone anchor 901 (a shank of the bone anchor is not visible in the embodiments as it is fully immersed in the bony material of a respective pedicle of vertebrae 100).

It is noted that the extension 9 in this embodiment is not considered a part of the rod insertion device 1. However, according to other embodiments, the extension 9 may be part of the rod insertion device. Extension devices, such as the extension 9, primarily serve to assemble parts to a bone anchor and facilitate final fixation but may herein additionally be used to define the position of the bone anchor to which it is mounted relative to the adapter and, thus, to the rod insertion device 1.

In the following, the above-described ingredient parts of the rod insertion device will be described in detail in FIGS. 2 through 22 and reference of their function will be taken with respect to the method steps illustrated in FIGS. 23 through 34.

The adapter 2 and its detail parts are illustrated in FIGS. 2 through 7. The adapter 2 includes a cuboid body 21 with substantially flat sidewalls 22 and rounded edges. The cuboid body 21 has an inner bore 281 which is dimensioned to slidingly receive an upper part of one of the extensions 9, 9', or 9" shown in FIG. 1. Within the bore 281, a flat portion 283 is formed which serves to guide respective flat portions 92, 92', 92" of the extensions. Due to the flat portion 283, rotation of the adapter 2, when attached to the extension 9, is prevented and the orientation of the rod insertion device 1 when assembled together is predefined with respect to the bone anchor 901.

At an upper end of the bore 281, an opening 24 towards the top face of the adapter 2 is formed which allows access to the bore. A small shoulder 282 (see FIG. 4) serves as an abutment for the adapter 2 with respect to an upper end of the extension 9.

As illustratively shown in FIGS. 23 and 24, in a method of using the rod insertion device 1, the first two steps of attaching the adapter 2 to the extension 9 are illustrated. Thereby, in FIG. 23, the adapter 2 is slid (see numeral 1023) onto a distal end of the extension 9. In FIG. 24, a step of securing the adapter 2 on top of the extension 9 using a securing plate 25 is illustrated as numeral 1024. The securing plate 25 is shown in more detail in FIGS. 6 and 7. The securing plate 25 includes a plate portion 255 that is dimensioned to be slid into a slot 29 of the adapter 2. A plate-shaped operating portion 251 allows the securing plate to be pushed into the slot 29 against a biasing force of a spring 26 which is attached to a nose 253 (see FIG. 6), and the operating portion 251 abuts a face 284 within an opening 28 (see FIG. 5).

An inner, almost circular opening 254 formed within the plate portion 255 allows the top portion of the extension 9 to be introduced therethrough when it is slid upwards within the bore 281 of the adapter 2. For this purpose, the securing plate 25 may be retained in position by introducing a pin 27 into hole 270 formed in the top face of the adapter 2. Thereby, a tip of the pin 27 enters into engagement with an opening 252 formed in the plate portion 255 of the securing plate 25 (see FIG. 6). Once the top portion of the extension 9 abuts the shoulder 282 at the upper end of the bore 281, a partially circular recess 91 formed in the upper portion of extension 9 faces the securing plate 25, such that, by virtue of the spring 26, the securing plate 25 is urged into and against the recess 91 of the extension 9, i.e., the securing plate 25 latches into recess 91, thereby fixing and securing the adapter 2 on the extension 9.

As shown in FIG. 2, the adapter 2 has grooves 23*a*, 23*a*', 23*b*, 23*b*' in opposing sidewalls 22 (e.g., sides) thereof. As will be described below, each of these grooves form part of a support structure for supporting the base portion 4 of the holding device 3 shown in FIG. 1. In the installed state of the adapter 2, the flat side surfaces 22 (e.g., sidewalls) in which these grooves are formed are oriented in a direction transverse to a line defined by the arrangement or row of the bone anchors 901 and the extensions 9, 9', 9".

As shown in FIGS. 8-10, which detail the holding device 3 and the rod guide 6 with the handle 7, the holding device 3 includes the base portion 4 which includes a main wall 40 and two sidewalls 41, 42 forming a U-shape which, upon attachment to the adapter 2, embrace the same at sidewalls 22. The sidewall 41, shown on the left side in the figures, includes two pins 43*a*, 43*b* at its distal end, and the right sidewall 42 includes two pins 43*a*', 43*b*' at its distal end. These pins are designed and shaped to respectively fit into grooves 23*a*, 23*b*, 23*a*', and 23*b*' of the adapter 2.

As can be seen in FIG. 25, showing a third step of using the rod insertion device 1, the base portion 4 may be attached to the adapter 2 (see numeral 1025) by inserting the pins 43*a*, 43*b*, 43*a*', and 43*b*' into upper ends of the grooves 23*a*, 23*b*, 23*a*', and 23*b*', respectively, from a top side of the adapter 2.

As can be seen in FIG. 26, which shows a fourth step of using the rod insertion device 1, the pins of the base portion smoothly slide within the grooves in the sidewalls 22 of the adapter 2. Upper portions 231*a* and 231*b* of respective grooves 23*a* and 23*b* (see FIG. 2) have a slightly curved but almost linear shape, such that an almost translational, vertical movement (see numeral 1026) of the holding device 3 and the rod guide 6 occurs. Thereby, the arrangement of the holding device 3 and the rod guide 6 held by the clamping portion 5 is such that a front portion 64 of the rod guide 6 (see FIG. 1) is oriented substantially parallel to the extension 9 and perpendicular to a skin surface (not shown) of the patient to allow an effective cut by a tip 81 of the cutting piece 8 (shown in FIGS. 18 and 19) protruding from the front portion 64 of the rod guide 6, to be further described below. Moreover, the translational movement 1026 allows an incision into the soft tissue that is close to the position of the bone anchor 901 and the extension 9.

As shown in FIG. 27, which shows a fifth step of the method in which a cutting edge 811 of the tip 81 has entered the soft tissue (not shown), the pins 43*a*, 43*b*, 43*a*', 43*b*' have entered a bottom section 232*a*, 232*b* (e.g., an end portion) of the grooves 23*a* and 23*b* (see FIG. 2) which are elliptically curved such that the holding device 3 and the rod guide 6 perform a pivoting movement 1027. The curvature of the pivoting movement almost corresponds to the curvature of the tubular rod guide 6. As a consequence, the rod guide 6 is introduced at a small incision point in the skin surface and soft-tissue ensuring the well-known advantages of minimally invasive surgery (MIS).

As shown in FIG. 28 showing a sixth step of the method, the front portion 64 of the rod guide 6 has attained or reached a position proximal to the receiving part 90 and the rod channel (not shown) formed therein. At this stage, the pins 43*a*, 43*b*, etc. of the base portion 4 have also reached ends of their respective tracks in the grooves 23*a*, 23*b*, etc., where stops may be arranged to indicate and give a tactile response to the operator that an end position has been reached. At this stage, the cutting piece 8, which is more detailed in FIGS. 18 and 19, may be removed using handle 84. The inner cutting piece 8 is formed of a curved rod having the tip 81 with the cutting edge 811 and an intermediate stop 83 (e.g., abutment) which ensures that only the tip 81 protrudes from the front portion 64 of rod guide 6 in the inserted state. The curvature of the cutting piece 8 corresponds to that of a curved tube portion 60 of the rod guide 6.

Next, the clamping portion 5 of the holding device 3 will be explained with regard to FIGS. 8 through 16. The clamping portion includes two brackets 51, 52 which are pivotably connected to a hinge 45 provided at an intermediate wall portion 44 (e.g., a main wall) of the base portion 4. In this specific embodiment, the hinge is formed of upper and lower eyelets 46, 47 (e.g., holes) formed in respective protrusions from the main wall 44 and a bolt 48 which can be inserted into these holes. The brackets 51, 52 include eyelets 56, 57 at their ends, respectively, which may be brought into alignment with eyelets 46, 47 of the main wall 44. The brackets 51, 52 may be pivoted about the hinge 45 towards and away from each other.

The left-side bracket 51 includes a partial semi-spherical recess 58, and the right-side bracket 52 also includes a partial semi-spherical recess 59 which are aligned with each other and have substantially the same size and radius, such that, when flat end faces 511, 521 of the brackets 51, 52 abut each other, the semi-spherical recesses 58, 59 form a substantially spherical, inner space leaving small openings at the upper and lower ends thereof to allow the rod guide 6 to extend therethrough, as will be further explained below. As becomes apparent from FIGS. 8 and 9 in conjunction with FIG. 1, this spherical, inner space is configured to receive a spherical, ball-shaped portion 61 of the rod guide 6. Thereby, the dimensions of the spherical, ball-shaped portion 61 may be, for example, slightly larger than those of the semi-spherical recesses 58, 59, such that a clamping function may be achieved when a first locking arrangement 53 (e.g., a first locking device) is tightened. Nevertheless, the dimensions of the spherical, inner space and the ball-shaped portion 61 may be identical. Details of the first locking arrangement can be seen in FIG. 12.

More specifically, the first locking arrangement 53 includes a hinged support 531 (e.g., a hinge) provided at the right-side bracket 52 which is formed as a single piece with a threaded shaft 532. The threaded shaft 532 may engage an internal thread 533 formed in a nut 534. Upon clamping the ball-shaped portion 61 of the rod guide 6, parts 531-534, which together form a tensioning screw, are pivoted about the hinge 531 to insert the shaft 532 into a recess 535 formed at an end of the left-side bracket 51, after which the nut 534 may be tensioned (e.g., tightened) into a form-fit groove 536 to obtain a secure connection, as shown, in particular, in FIG. 12.

As can be seen in FIG. 31, further described below, the first locking arrangement 53 allows the brackets 51, 52 to be completely removed from around the ball-shaped, spherical portion 61 by pivoting the brackets away from each other.

The clamping portion 5 (e.g., a clamping device) of this embodiment includes a second locking arrangement 54 (e.g., a second locking device), which is shown in more detail in FIGS. 9, 11, and 16.

As can be best seen in FIG. 11, the second locking arrangement 54 may serve to fix the position and orientation of the ball-shaped, spherical portion 61 of the rod guide 6 within the inner, spherical space defined by the semi-spherical recesses 58, 59 of the brackets 51, 52, respectively. For this purpose, the second locking arrangement includes a nut 544, into which a latching pin 541 is attached (e.g., press-fit or threaded), and which is shown in more detail in FIG. 16. The latching pin 541 has a generally cylindrical shape except for a shoulder 547 and a nose 548 formed at its distal end. A coil spring 543 may be fitted over the cylindrical portion of the latching pin 541 to abut the shoulder 547 on the one side and an inner, annular shoulder 546 formed by undercut bore 514 which is provided in the left-side bracket 51. As a consequence, as can be seen in FIG. 11, the latching pin 541 is urged by the coil spring 543 towards the semi-spherical recess 58 and—if the spherical ball-shaped portion 61 of the rod guide 6 is inserted—into a bore 62 formed therein.

Thereby, the nose 548 provided at the distal end of the latching pin 541 is designed to fit into a respective recess 621 formed in the bore 62 when the latching pin attains a specific orientation.

As can be seen in FIGS. 9, 11, and 16, a pin 542, fitted into a respective hole 545 of the latching pin 541 and protruding from both ends of the hole 545, may latch either into a recess 512 positioned remote from the semi-spherical recess 58 or into a recess 513 which is closer to the semi-spherical recess 58 (see FIGS. 14 and 15). The recesses 512, 513 define two different indexing positions for the latching pin 541 such that, when the pin 542 is latched into the recess 512, the distal end of the latching pin 541 (the nose 548) does not protrude into the semi-spherical recess 58, and when the pin 542 latched into the recess 513, the distal end of the latching pin 541 protrudes into the semi-spherical recess 58 or into the bore hole 62 of the spherical ball-shaped portion 61 of the rod guide 6 to fix the same. Because the latching pin 541 is urged towards the inner spherical space defined by the recesses 58, 59, the operator has to pull the nut 544 outwards (e.g., away from the recesses 58, 59) in order to switch between the locked state and a released state with respect to the spherical, ball-shaped portion 61.

An overview of the rod guide 6 with the handle 7 is given in FIGS. 20-22. The handle 7 of this embodiment can be removed from the rod guide by a button 71. The rod guide 6 includes the curved tube portion 60 having an inner bore 67 whose diameter may correspond to that of a stabilization rod 95, and the front portion 64 defining an exit from the tube. The spherical, ball-shaped portion 61 is provided at an upper part of rod guide 6, and the curved tube portion 60 extends therefrom. The curved tube portion is fitted into an annular extension 63 provided at a lower portion of the spherical, ball-shaped portion 61. The inner bore 67 extends through the spherical, ball-shaped portion 61 up to an opening 65 (e.g., an entry hole) formed in a rear part 66 of the rod guide and defining an entry for the stabilization rod into the inner bore 67. The rear part 66 of the rod guide 6 provides for a connection to handle 7.

Returning to the description of the method of using the rod insertion device 1, FIG. 29 shows a seventh step and a state in which—after having removed the inner cutting piece 8,—the arc-shaped or curved spinal stabilization rod 95 is inserted into the entry hole 65 formed in the rear part 66 of the tubular rod guide 6 (see numeral 1029) and advanced into the inner bore 67. Details of the tubular rod guide 6 are shown in FIGS. 20 through 22. The spinal stabilization rod 95 is advanced until its tip exits from the inner bore 67 of the curved rod portion 60 at the front portion 64 of the rod guide 6 in this step.

This state is depicted in FIG. 30, which shows an eighth step of the method of using the rod insertion device 1. While upon further advancing (numeral 1029) the spinal stabilization rod 95 into and through the rod channel of the receiving part 90, an operator may choose to adapt (e.g., change) the orientation of the spinal stabilization rod 95 and the rod guide 6. Therefore, the nut 544 of the second locking arrangement 54 is pulled and rotated (see numeral 1030*b*) in order to retract the latching pin 541 from the bore 62 of the spherical, ball-shaped portion 61 of the rod guide 6. Because the spherical, ball-shaped portion 61 may still be clamped by the tensioning screw of the first locking arrangement 53, the nut 534 of the tensioning screw is slightly rotated to reduce the tensioning force (see numeral 1030*a*). As a consequence, the fixation of the rod guide due to the second locking arrangement 54 and the clamping due to the first locking arrangement 53 is lifted, while the spherical ball-shaped portion 61 is still supported by (e.g., contained within) the spherical, inner space formed by the recesses 58 and 59. As a result, the spherical, ball-shaped portion 61 functions like a ball joint, allowing polyaxial pivoting movements (see numeral 1030c) and corrections of the 3D-orientation of the rod guide 6 within the spherical, inner space.

The annular extension 63 at one side of the spherical, ball-shaped portion 61 as well as the rear part 66 at the other side of the spherical, ball-shaped portion 61 allow for a sufficient degree of pivoting as can best be seen in FIG. 11.

FIG. 31 shows a ninth step of the method of using the rod insertion device 1. The advancement (numeral 1029) of the spinal stabilization rod 95 continues with its tip entering a rod channel of the second receiving part 90' of the second bone anchor 901. Occasionally, the operator may want to apply a greater degree of re-orientation and gain a greater degree of control over further advancement of the spinal stabilization rod 95. For this purpose, the operator unscrews the tensioning screw (parts 531-534 shown in FIG. 9) and releases the tensioning screw from the recess 535 and the groove 536. As a consequence, the brackets 51 and 52 may be pivoted (see numeral 1031) and move away from each other to fully release the rod guide 6 from the spherical, inner space formed by the recesses 58, 59.

As the holding device 3 is no longer needed, the base portion 4 with the clamping portion 5 may be pushed upward with the pins 43a, 43b, 43a', 43b' sliding through the respective grooves 23a, 23b, 23a', 23b' to be removed from the adapter 2. The state is depicted in FIG. 32, which shows a tenth step of the method of using the rod insertion device 1. The operator may control further alignment 1029 by just exerting forces via handle 7 onto the rod guide 6. As an example, the spinal stabilization rod 95 is further advanced through the third receiving part 90" which may not be in-line with the first and second receiving parts 90, 90' in this specific embodiment.

As shown in FIG. 33, which shows an eleventh step of the method, the handle 7 with the rod guide 6 may be removed from the end of the rod 95 after the same has been fully brought into place. After performing a further step (not shown) of providing set screws, etc. through the inner bores of the extensions 9, 9', 9" towards the receiving part in order to fixate the spinal stabilization rod 95 within the rod channels, an unused end portion 95a may be removed by separating (see numerals 1034a) the same from the inserted rod 95 at a predetermined breaking point 96 (see also FIG. 34 which illustrates a twelfth step of the method). The unused rod end 95a may be drawn out (see numeral 1034b) of the soft tissue. At this stage, the adapter 2 is also removed from the first extension 9.

The first and second locking arrangements 53 and 54 of the clamping portion 5 according to the first embodiment advantageously facilitate two different states of releasing the rod guide 6 from the clamping portion 5. The operator can selectively control the advancement of the spinal stabilization rod through the rod channels by selecting between a predetermined insertion path when the rod guide is clamped and fixed, in which state partial release and polyaxial re-orientation of the rod guide is possible, and full release from the holding device depending on the situation. Polyaxial corrections are thus applied with less effort, and the method of inserting a rod is simplified. On the other hand, a secure insertion is improved since the operator may have full control over the insertion process.

A second embodiment of the invention will be described with reference to FIGS. 35 and 36. Like numerals denote the same parts as in the first embodiment and will not be described repeatedly. A main difference of the rod insertion device 1' of the second embodiment with respect to the first embodiment is seen in the clamping portion 5'. Herein, first and second brackets 51' and 52' are not provided as pivoting parts but as being translationally movable or slidable towards and away from each other.

Therefore, protruding pins 537 of the first bracket 51' are provided to be inserted into respective holes in the second bracket 52'. By virtue of undercuts 538, the connection between the brackets 51', 52' is locked by inserting a locking plate 536 of a first locking arrangement 53', which corresponds in function to the first locking arrangement 53 of the first embodiment, into a slot 536a, such that, when the locking plate 536 is lifted, a recessed portion 539 of the locking plate 536 engages with the undercuts 538.

The function of a second locking arrangement 54' is similar to that of the second locking arrangement 54 of the first embodiment.

In use, the locking position of the locking plate 536 is ensured by the annular abutment 83 of the inner cutting piece 8 (see FIG. 18). This is because the locking plate 536 has an upper flange which latches onto the annular abutment 83. Having cut a path through the soft tissue using the cutting edge 811 at the tip 81, the cutting piece 8 may be lifted by the handle 7 to remove the same. As a consequence, the abutment 83 is removed and the locking piece 536 may be slid further into slot 536a such that the protruding pins 537 are released from the second bracket 52' (i.e., the recessed portion 539 disengages from the undercuts 538). Further advancement of the rod guide 6 and the spinal stabilization rod 95 into the soft tissue may now be performed manually as the path has been predefined.

The materials employed for each of the parts in the embodiments described above may be selected from metals, such as stainless steel, titanium, nickel, and/or titanium alloys, etc., or from plastic materials as long as certain durability and rigidity conditions are met and bio compatibility is guaranteed.

The stabilization rod 95 may also be made from biocompatible metals or plastics. In one embodiment, the rod has a curvature which corresponds to that of the rod guide.

The invention also provides for an embodiment including the rod inserter as described above wherein two or more rod guides are provided which differ from each other by the radius of curvature of their respective curved tube portions 60. Corresponding rods having appropriate curvatures may then also be selected according to the application.

Several modifications of the above embodiments may be made without departing from the scope of the invention as defined in the appended claims.

For example, fixation means other than the above-described tensioning screw or indexing pin may be used to clamp, lock, and fixate the rod guide in the clamping portion.

Moreover, instead of the support structure defined as pairs of grooves and pins sliding therein, a hinge mechanism may be provided and/or a single rotation axis may be employed to facilitate the pivoting movement of the holding device and the rod guide.

Further, parts such as the handle 7 or the inner cutting piece 8 may be omitted.

Still further, the bone anchors and extensions to which the present rod insertion device is applied may be of various types, for example, the bone anchors may be embodied as polyaxial bone anchors or monolithic bone anchors and the shape and design of the rod channels may be selected from a variety of categories known in the art.

The invention claimed is:

1. A rod insertion system and at least two bone anchors, one of the at least two bone anchors comprising a receiving part having a rod channel, the rod insertion system comprising:
   an extension configured to be mounted to the receiving part;
   a tubular rod guide configured to accommodate a spinal stabilization rod therein;
   a holding device comprising a clamping portion configured to hold a portion of the rod guide; and
   an adapter configured to be connected to the extension and configured to movably support the holding device,
   wherein, in a first state in which the adapter is connected to the extension and the rod guide is fixed to the holding device by the clamping portion, the holding device is configured to move and pivot along the adapter, and
   wherein, in a second state in which the holding device supports the portion of the rod guide, the clamping portion is sufficiently released from the portion of the rod guide to permit an orientation of the rod guide relative to the holding device to be polyaxially adjusted.

2. The rod insertion system of claim 1, wherein the tubular rod guide is curved.

3. The rod insertion system of claim 1, wherein, in a third state, the clamping portion is fully released from the portion of the rod guide to permit the orientation of the rod guide relative to the holding device to be freely adjusted.

4. The rod insertion system of claim 1, wherein
   the clamping portion has an inner, spherical space,
   the portion of the rod guide to be held by the clamping portion comprises a spherical, ball-like portion, and
   the spherical, ball-like portion fits into the inner, spherical space of the clamping portion.

5. The rod insertion system of claim 4, wherein the clamping portion comprises a pair of brackets and a first locking arrangement, and each of the brackets comprises a hollow, semi-spherical recess,
   wherein, when both of the brackets are locked with each other by the first locking arrangement, the semi-spherical recesses are aligned with each other and closed to form the inner, spherical space, and
   wherein, when the first locking arrangement is unlocked, the semi-spherical recesses are configured to be separated from each other and the inner, spherical space opened.

6. The rod insertion system of claim 5, wherein the first locking arrangement comprises:
   a tensioning screw pivotably supported at one of the brackets and configured to latch into a corresponding recess in the other one of the brackets.

7. The rod insertion system of claim 5, wherein each of the brackets are pivotably supported at a base portion of the holding device to open and close the inner, spherical space.

8. The rod insertion system of claim 5, wherein each of the brackets are configured to be joined with and separated from each other in a linear direction to open and close the inner, spherical space.

9. The rod insertion system of claim 5, wherein the clamping portion further comprises a second locking arrangement which is configured to fix an orientation of the spherical, ball-like portion of the rod guide within the inner, spherical space of the clamping portion.

10. The rod insertion system of claim 9, wherein the second locking arrangement comprises:
    an indexing pin retractably insertable into a bore hole in the spherical, ball-like portion of the rod guide, the indexing pin being configured to fix the orientation of the spherical, ball-like portion of the rod guide within the inner, spherical space of the clamping portion.

11. The rod insertion system of claim 1, further comprising a cutting piece comprising a cutting tip, the cutting piece being configured to be inserted into the rod guide to cut a path into a soft tissue.

12. The rod insertion system of claim 1, further comprising a handle attached to the rod guide to facilitate moving and pivoting of the holding device.

13. The rod insertion system of claim 1, wherein the adapter further comprises a support structure for movably supporting the holding device, and
    wherein the support structure defines a moving path for the holding device.

14. The rod insertion system of claim 13, wherein the support structure comprises at least two grooves in a sidewall of the adapter, the at least two grooves being configured to receive and slidably engage pins protruding from a base portion of the holding device.

15. The rod insertion system of claim 14, wherein the grooves are configured to urge the rod guide held by the holding device to first move substantially linearly along and parallel to the extension and then pivot along a curved path towards the receiving part of the bone anchor.

16. The rod insertion system of claim 1, further comprising another rod guide having a curvature different than that of the rod guide to facilitate insertion of stabilization rods having different curvatures.

17. The rod insertion system of claim 1, wherein the extension and the adapter are configured to be detachably connected to each other.

18. The rod insertion system of claim 1, wherein the holding device further comprises a base portion,
    wherein the clamping portion is coupled to the base portion, and
    wherein the base portion of the holding device is configured to move and pivot along the adapter.

19. The rod insertion system of claim 18, wherein the base portion is configured to move along the adapter in an extending direction of the extension such that the holding device and the rod guide approach the receiving part, and
    wherein the base portion is configured to pivot along the adapter such that, as the base portion pivots along the adapter, a portion of the holding device farther from the adapter moves a greater distance than a portion of the holding device nearer to the adapter.

20. The rod insertion system of claim 1, wherein the rod guide has an opening at each of a proximal end and a distal thereof, and
    wherein, in the first state, one of the openings of the rod guide is configured to be located proximal the rod channel of the receiving part such that a tip of a spinal stabilization rod passing through the openings of the rod guide will enter the rod channel of the receiving part.

21. The rod insertion system of claim 20, wherein, in the second state, one of the openings of the rod guide is proximal to the rod channel of the receiving part.

22. The rod insertion system of claim 1, wherein, in the first state, the holding device is configured to move and pivot along the adapter such that a front portion of the rod guide is positioned proximal to the rod channel of the receiving part.

23. A rod insertion device for inserting a spinal stabilization rod into at least two bone anchors, the rod insertion device comprising:
a rod guide configured to accommodate a spinal stabilization rod therein;
a holding device comprising:
a base portion; and
a clamping portion coupled to the base portion, the clamping portion comprising a first locking device and a second locking device, the clamping portion being configured to support a portion of the rod guide, and the first locking device being configured to clamp the clamping portion onto the portion of the rod guide; and
an adapter configured to moveably support the holding device,
wherein, in a first state, the second locking device is engaged with the rod guide to fix the rod guide to the clamping portion, and
wherein, in a second state, the holding device supports the portion of the rod guide and the second locking device is disengaged from the rod guide to permit an orientation of the rod guide relative to the clamping portion to be polyaxially adjusted.

24. The rod insertion device of claim 23, wherein the clamping portion comprises a plurality of brackets, and
wherein the first locking device is configured to clamp the plurality of brackets onto the portion of the rod guide.

25. A method for inserting a spinal stabilization rod into at least two bone anchors utilizing a rod insertion system, the rod insertion system comprising a first bone anchor and a second bone anchor, each of the first and second bone anchors having a receiving part having a rod channel; an extension configured to be mounted to the receiving part of the first bone anchor; a tubular rod guide configured to accommodate a spinal stabilization rod therein; a holding device comprising a clamping portion configured to hold a portion of the rod guide; and an adapter configured to be connected to the extension and configured to moveably support the holding device, wherein, when the adapter is connected to the extension and the portion of the rod guide is supported by the holding device, the holding device is configured to move and pivot along the adapter such that a front portion of the rod guide is positioned proximal to the rod channel of the first bone anchor, wherein, in a first state, the rod guide is fixed to the holding device by the clamping portion, and wherein, in a second state in which the holding device supports the portion of the rod guide, the clamping portion is sufficiently released from the portion of the rod guide to permit an orientation of the rod guide relative to the holding device to be polyaxially adjusted, the method comprising:
in the first state, inserting the holding device into grooves at a top end of the adapter;
sliding the holding device along the grooves in the adapter such that the holding device moves and pivots to cut soft tissue and positions a distal end of the rod guide proximal to the rod channel of the first bone anchor;
inserting the spinal stabilization rod into a proximal end of the rod guide; and
advancing the rod through the rod guide and into the rod channel of the first bone anchor.

26. The method of claim 25, further comprising:
sufficiently releasing the clamping portion from the portion of the rod guide to enter the second state; and
in the second state, further advancing the rod into the rod channel of the second bone anchor.

27. The method of claim 26, wherein the rod insertion system further comprises a third bone anchor having a receiving part having a rod channel; and a third state in which the rod guide is fully separated from the holding device, the method further comprising:
further releasing the clamping portion to release the rod guide from the holding device to enter the third state; and
further advancing the rod into the rod channel of the third bone anchor.

28. The method of claim 27, further comprising:
fixing the rod into the receiving part of each of the bone anchors; and
separating an unused portion of the rod from a fixed portion of the rod.

29. The method of claim 25, further comprising attaching the adapter to the extension prior to the inserting the holding device into the grooves.

30. The method of claim 25, wherein a cutting piece is inserted into the rod guide prior to the inserting the holding device into the grooves.

31. The method of claim 30, further comprising:
removing the cutting piece from the rod guide after the sliding the holding device along the grooves.

* * * * *